United States Patent [19]
Ericsson

[11] Patent Number: 5,773,241
[45] Date of Patent: Jun. 30, 1998

[54] PREPARATION OF BIOACTIVE EXTRACTS

[76] Inventor: Arthur Dale Ericsson, 6560 Fannin, Suite 720, Houston, Tex. 77030

[21] Appl. No.: 854,473

[22] Filed: May 12, 1997

Related U.S. Application Data

[63] Continuation of Ser. No. 708,548, Sep. 5, 1996, abandoned.

[51] Int. Cl.$^6$ ............................. A61K 35/00; C12P 1/00
[52] U.S. Cl. ..................... 435/41; 424/115; 424/123; 435/41; 435/156; 435/171; 435/408
[58] Field of Search ................................. 435/171, 156, 435/41, 408; 424/115, 123

[56] References Cited

U.S. PATENT DOCUMENTS

| | | | |
|---|---|---|---|
| 3,801,459 | 4/1974 | Colton et al. | 435/127 |
| 5,340,729 | 8/1994 | Krummenacher | 435/171 |

OTHER PUBLICATIONS

APS Abstract Tominaga Japanese Patent 55–71470 (May 29, 1980) Preparation of Seasoning, Aug. 1980.
Derwent Abstract 97–23915/22 JP09075031 (Mar. 1997) Sunbase Fodd KK.

*Primary Examiner*—Herbert J. Lilling
*Attorney, Agent, or Firm*—John R Casperson

[57] ABSTRACT

This invention relates to the extraction of biological compounds from plants and animals and to the preparation and tinctures and essences from the extracted materials. The materials are extracted using alcoholic and/or phosphate buffered saline solutions. The extraction step can be performed repeatedly on the residue from the previous step. The rich solution resulting from the extraction can be freeze dried for further use or employed as a fermentation feed. The fermenter product can be freeze dried for further use. The invention also makes use of the residues resulting from the extraction and fermentation reactions.

24 Claims, No Drawings

PREPARATION OF BIOACTIVE EXTRACTS

This application is a continuation of application Ser. No. 08/708,548, filed Sep. 5, 1996, now abandoned.

BACKGROUND OF THE INVENTION

This invention relates to the extraction of biological compounds from plants and animals and to the preparation and tinctures and essences from the extracted materials.

Theophrastus Bombastus von Hohenheim (Paracelsus 1493–1541) prepared a large part of his medications by a process of extraction and labeled it the Spagyric process. This process was described in ancient China, India and Egypt. However, many of the preparations lacked high potency. A more complete extraction process would result in higher potency medications.

Many chemical species found in nature are in the process of transmutation. Many combinations of chemical elements exist dynamically in nature, moving toward a homeostatic state. In fact, many bioactive chemical compounds exist in nature, as dextrorotary, levorotary and mesorotary forms; each with the same number of atoms and each with different biochemical properties. A process of extracting a specific active principal from mixtures found in nature would be very desirable.

OBJECTS OF THE INVENTION

It is an object of this invention to provide a more complete extraction process for plant and animal material.

It is another object of this invention to provide a method of preparing extracts which considers and incorporates the basic principles of parachemical formulas in which the aggregate fractals of chemical substances are obtained from plants and animals.

It is a further object of this invention to provide a process of extraction which is a projection of the natural chemical process; in which the transformation is completed by a chemical method of throwing upon it, i.e. projecting, a specific active principle.

SUMMARY OF THE INVENTION

In accordance with one embodiment of the invention, a plant or animal material is provided in a finely divided form suitable for extraction. The finely divided plant or animal material is extracted in an extraction zone using a solvent to produce a rich solvent and an extract residue. A fermentation feed is formed from the rich solvent and fermented to produce a fermentation broth comprising a fermentation liquid and a fermentation residue. The fermentation liquid is separated from the fermentation residue and concentrated to produce a concentrate which can subsequently be used to form medicaments.

In accordance with another embodiment of the invention, a plant or animal material is provided in a finely divided form suitable for extraction. The finely divided plant or animal material is extracted in an extraction zone using a solvent to produce a rich solvent and an extract residue. The extract residue is subjected to extraction twice more, and the resulting rich solvents are combined and concentrated by freeze drying to produce a concentrate. The process produces a concentrate having a high potency due to the serialized extraction technique.

The concentrate can be reconstituted to produce a tincture by the addition of a solvent. An essence can be prepared from the tincture by distilling a portion of the solvent from the tincture and recovering the distillate. The distillate will be enriched in the volatile constituents of the concentrate.

Alternatively, an essence can be prepared by fermenting a finely divided plant material in the presence of water in a fermentation zone to produce a fermentation liquid. A distillate is recovered from the fermentation liquid by vacuum distillation. An alcohol is added to the distillate to produce the essence.

DETAILED DESCRIPTION OF THE INVENTION

The provision of a plant or animal material in a form suitable for extraction can take a variety of routes. Plants when collected from their natural habitat are called "wild crafted", but when grown commercially, using natural and organic techniques, are known as cultivated. Preferably, only healthy organic and naturally grown plants and animals are used in the inventive process. These are grown without the addition of artificial fertilizers, pesticides, hormones, genetic alterations and/or inoculations.

Botanical sources include whole plants, leaves (folia), herbs (herbae), buds (gemmae), flowers (flores), stems (stipites), barks (cortices), woods (ligna), roots (radices), fruits (fructi), seeds (semina) and berries (baccase). Plants are usually collected during the flowering season, cleansed by shaking (preferably in natural water), gentle rubbing, or brushing. Leaves and the aerial parts are collected when they are fully developed, usually shortly before the flowering season. Flowers and flowering tops of plants are preferably collected when they are just about to open and usually during dry weather. Stems and barks of resinous trees are preferably cut after the development of the leaves, while the non-resinous barks are preferably collected in the autumn from young trees. Woods are preferably gathered in the early spring, before the sap rises. Roots and rhizomes of annuals are preferably collected in the autumn while those of biennials are preferably dug in the spring and those from perennials are preferably collected in the second or third year of growth. Fruits, seeds and berries are preferably gathered when they are ripened.

After harvesting, most herbs and plants have a moisture content of 60–80% and are unsuitable for storage without some form of drying. The reason for drying plants is to prevent chemical decomposition and bacterial and fungal contamination of the specimens. Commercially, most herbs are dried at a temperature of 100–140 degrees F. By this method, the proper final moisture content is preferably reduced to less than 14%.

Garbling is a term that is used for the process of separation of the part of the plant to be used for extraction from the other parts of the plant that has been harvested inadvertently. This step is usually performed during the harvesting phase but may be performed at any stage prior to grinding.

Grinding or mincing a plant or herb means that the harvested botanical is mechanically broken down into smaller units, ranging from larger course fragments to a fine powder. The most common machine to be used is the hammer mill, knife mill and teeth mill. Preferably, the comminution step is followed by a fine grinding step, for example, in a commercial blender to reduce the plant part to the smallest particles possible without damaging the bioactive ingredients. In this manner, the surface area of each particle is increased and, therefore, the opportunity for more complete extraction of the vital chemical substances is enhanced.

For animal materials a natural or organically grown animal is preferably sacrificed in an acceptable manner. The organs and/or glands to be harvested are dissected, in an aseptic manner, preferably by a surgeon or veterinarian or animal surgical technician whose skills include animal anatomy and animal surgery. The harvested materials are then preferably carefully cleaned from any attachments of fat, capsules(s), blood vessels, and/or other attachments and the solid is then washed, preferably with a sterile phosphate buffer solution as hereinafter described. The thus cleaned material is then cut and sterile macerated by dissection and finally by the use of a sterile commercial blender.

In one embodiment of the invention, a finely divided plant material, such as that previously described, is fermented in the presence of water in a fermentation zone to produce a fermentation liquid. Preferably spring water is used, and the plant material is chopped or macerated promptly after gathering. A loosely covered container forms a suitable fermentation zone. When the gas of fermentation ceases, the fermentation is complete. A distillate is then recovered from the fermentation liquid by low temperature technique, such as by vacuum distillation. An alcohol, preferably ethanol, is added to the distillate to produce the essence. The addition of ethanol to provide the essence with a 15% concentration of ethanol will provide good results.

If desired, a residue can be recovered from the fermentation liquid, such as by centrifugation. The residue can be dried to provide a dried residue, which can be incinerated and/or calcined for further use. Also, essential oils can be removed and collected for further use. When the finely divided plant material is mixed with water, a mixture containing essential oils is produced. These essential oils can be separated from the mixture to form a deoiled fermentation feed which is introduced into the fermentation zone.

Usually, yeast is added to the fermentation zone to drive the fermentation reaction. A fermentable sugar can also be introduced into the fermentation zone. A quantity of 500 grams of sugar for every 2–3 kilograms of fresh plants is suitable. Upon completion of the fermentation, it is preferred to separate the fermentation liquid from the finely divided plant material to produce a clarified liquid which is then distilled. Generally speaking, about 100 grams of plant material can be expected to yield about a kilogram of distillate.

The calcined residue contains salts which can be extracted, using distilled water, for example. The extracted salts can then be combined with the distillate for increased potency. The salts can be added to the distillate and the mixture vigorously shaken or the distillate can be poured over the salts and the mixture then shaken to form a solution.

The potency of the essence can be further increased by gentle stirring. Rotation of the flask of an essence is called pelicanization or circulation, and is particularly effective where the rotation is rhythmic. Good results can be obtained by carrying out the circulation, periodically, for one month.

In another embodiment of the invention a finely divided plant or animal material is extracted in an extraction zone using a solvent to produce a rich solvent and an extract residue. The process of extraction of herbs and plants is the separation, by physical and chemical means, of the desired chemical material from a plant by means of water, steam, alcohol or a solvent. The simplest process and the most common commercial practice consists of soaking the material in an alcohol/water solution for a period of time and then filtering the solid part from the solute. In this embodiment of the invention, the solute is subjected to fermentation and subsequently concentrated.

Preferably, the extract residue is subjected to extraction twice more, with the rich solvent resulting from each extraction step being subjected to fermentation. The extract residue is extracted using a solvent to produce a second rich solvent and a second extract residue. The second extract residue is extracted using a solvent to produce a third rich solvent and a third extract residue. The second rich solvent and the third rich solvent are combined together with the rich solvent to form the fermentation feed. The separation of solvent and extract residue can be by any suitable means, but is preferably centrifugation. The solvents can be the same for each stage. The extract residue can be incinerated and calcined for further use.

The solvent is preferably water based and contains an alcohol, preferably ethanol, and/or phosphate buffered saline. Essential oils are soluble to some extent in alcoholic solutions, while proteins and carbohydrates are soluble in buffered phosphate solutions. Where both ethanol and phosphate buffer is employed, the solvent can be characterized as containing water, ethanol, and chlorides and phosphates of sodium and potassium. For ground plant material, a mixture of ethanol and water will provide good results.

For macerated animal material, phosphated buffered saline alcohol solution (PBSA) is preferred. An exemplary solvent for the extraction of animal materials (or plant materials if desired) can be formed by adding 160 gm NaCl, 4 gm KCl, 23 gm $Na_2HPO_4$, and 4 gm $KH_2PO_4$ to 1000 ml of distilled water with heating and/or stirring until the solids are dissolved. This forms a phosphate buffer saline solution (PBS) which can be used as a solvent in accordance with the invention. The PBS can then be cooled and 500 ml 70% ethanol added to it. This forms the preferred PBSA solvent.

The extraction will sometimes result in the production of essential oils. Where the recovery of these oils is desired, they are separated from the fermentation feed to form a deoiled fermentation feed prior to introduction into the fermentation zone. The oils may be separated by boiling with simultaneous distillation of the steam and oils that are on the surface of the water or by vacuum distillation or by steam distillation. The oils are insoluble and float to the top of the distillate from where they can be recovered, for example, by skimming or absorption from the accumulator of the distillate condenser. For some extracts, a temperature of over 80° C. may be used, but for most the lower the temperature, the better, as both proteins and alkaloids are often destroyed by temperature. Moreover, the action of heat will further denature any of the amino acids and thus render sequencing of the amino acids inactive for the essential receptor activation/inhibition. It should be also be noted that many biological products are lipoproteins, proteins and glycoproteins which may be inactivated by the action of alcohol (denaturation) in the diluent. Therefore, excessive alcohol concentration should be avoided where it is desired to recover these materials in an active form.

Yeast, such as *saccharomvces aerevisiae*, is preferably brought together with the fermentation feed in the fermentation zone. A large glass flask corked with a small fermentation tube forms a suitable fermentation zone. About 20 grams of yeast per liter of fermentation feed is generally suitable. Preferably, a nutrient medium is also brought together with the fermentation feed in the fermentation zone. A suitable nutrient medium can be formed from yeast extract, peptone, magnesium salts, and glucose. Buffered phosphate solution can be employed as diluent. A fermentable sugar can also be included in the nutrient medium. When used, about 1 part by weight of pure fermentable sugar for each part by weight of liquid in the fermentation zone will provide good results. Preferably, the fermentation is allowed to continue, generally at 80°–90° F., until the production of gas substantially ceases.

After fermentation, the fermentation liquid is separated from the fermentation residue. The separation is facilitated by permitting the residue to settle and can be achieved by decanting, for example. Residual fermentation liquid can be recovered by centrifuging the fermentation residue. The fermentation residue can be either freeze dried or incinerated to produce an ash and the ash calcined. The calcined ash contains salts which can be extracted if desired such as with distilled water to form an aqueous salt-containing medium. If desired, the aqueous salt-containing medium can be combined with the fermentation liquid prior to concentration to enhance the potency of the concentrate.

The fermentation liquid can be concentrated by any suitable technique, such as by distillation or the use of thin film evaporators. However, freeze drying is preferred. Freeze drying is the process of removing moisture from a biological product under vacuum to preserve the integrity of the product's biological and chemical structure and functional activity. Preferably, the freeze drying process is carried out in three steps. First, a sublimation feed containing ice is prepared by pre-freezing the fermentation liquid. The step generally involved freezing the product below the eutectic temperature. The sublimation feed is then freeze dried to remove the ice from the sublimation feed and form a low moisture content product and alcoholic vapors. The low moisture content product comprises a dry, structurally intact botanical/biological product. This process requires the control of both temperature and pressure as the rate of sublimation of ice from a frozen product depends upon the difference in the vapor pressure of the product compared to the vapor pressure of the ice condenser. Molecules then migrate from the higher pressure sample to a lower pressure area. It is therefore important that the temperature at which a product is freeze dried be balanced between the temperature that maintains the frozen integrity of the product and the temperature that maximizes the vapor pressure of the product-optimum drying. The low moisture content product is then finish dried, generally at somewhat higher temperatures, under isothermal desorption conditions, preferably so as to reduce the moisture content of the finish dried product to less than about 7%. The resulting product is preferably in a solid or semisolid form. The alcoholic vapors resulting from the freeze drying process can be condensed to form a liquid if desired and recycled to the extraction zone.

In accordance with another embodiment of the invention, a plant or animal material is provided in a finely divided form suitable for extraction. The finely divided plant or animal material is extracted in an extraction zone using a solvent to produce a rich solvent and an extract residue. The extract residue is subjected to extraction twice more, and the resulting rich solvents are combined and to form a combined rich solvent which is concentrated by freeze drying to produce a concentrate. The extraction and freeze drying conditions can be as previously described. However, if desired, the rich solvent can be vacuum distilled from the extraction zone in preparation for freeze drying. Insoluble oils can be separated from the combined rich solvent prior to the freeze drying step. The residue resulting from the extraction can be either calcinated or freeze dried for further use. Alcoholic vapors produced during the freeze drying process can be condensed to a liquid and recycled to the extraction zone.

The concentrate can be reconstituted by the addition of a solvent to form a tincture. Preferably, the concentrate is reconstituted to the same concentration in which it was present in the fermentation liquid. For this reason, the volume of fermentation liquid charged to the freeze drying process should be noted. Classically, tinctures are prepared with the use of a 70% alcohol in sterile water. In accordance with the invention, however, the solvent used can be the same as was used in the extraction process. Generally speaking, the tincture comprises in the range of from about 2 to about 50 parts by weight of solvent for each part by weight of concentrate, usually in the range of 4 to 25 parts by weight of solvent for each part by weight of concentrate. All tinctures have a limited life span and, in time, their therapeutic value diminishes. They appear to last about a year. On the other hand, freeze dried preparation of tinctures appear to last indefinitely as long as they are not reconstituted.

Essences contain only the volatile constituents of the plants from which they are prepared, since they are always distilled. They have a longer life span than tinctures. An essence can be prepared from the tincture noted above by distilling a portion of the solvent from the tincture to produce the essence in the form of a distillate, and a residue. Preferably, the solvent comprises a 50–80 percent by weight ethanol solution, although a higher boiling solvent, such as PBS or PBSA can be used if a technique such as vacuum distillation is employed. Slow distillation under a vacuum at a low temperature in a fractionating flask and condenser to allow for maximum expansion of the vapors is preferred. The distillation can be terminated when the distillate no longer has a taste. Residual solvent can be removed from the residue, such as by evaporation, to form a dried residue which can be subsequently incinerated and/or calcined for subsequent use. The distillate can be pelicanized for greater efficacy.

SPECIFIC EMBODIMENTS

Plant Extraction Process
1. Plant material is prepared for extraction by harvesting, drying, garbling and grinding.
2. The resulting material is extracted with 70% ethyl alcohol by immersion for 3–7 days, followed by centrifugation, decantation and storage of the liquid in a container.
3. Step 2 is repeated on the solid material separated by centrifugation with the resulting liquid being added to the container.
4. Step 3 is repeated on the solid material separated by centrifugation with the resulting liquid being added to the container.
5. The solid material remaining from step 4 is calcinated and freeze dried for adding to a topical cream.
6. The liquid in the container is measured and freeze dried.
7. The freeze dried material resulting from step 6 is reconstituted to its original volume with PBSA.
8. Further dilutions may be made with PBSA in order to prepare the final medication solution.

Alternative Plant Extraction Process
1. Step 1 is as above.
2. Steps 2–4 are as above except that PBSA solution is used instead of ethanol solution and the liquid is separated by vacuum distillation rather than by decanting.
3. Steps 5–8 are as above.

Animal Extraction Process
1. Animal material is prepared for extraction by harvesting, cleaning and grinding under sterile conditions.
2. The resulting material is extracted with PBSA for 1 hour with constant agitated rotation, followed by centrifugation, decantation and storage of the liquid in a sterile container.
3. Step 2 is repeated on the solid material separated by centrifugation with the resulting liquid being added to the container.

4. Step 3 is repeated on the solid material separated by centrifugation with the resulting liquid being added to the container.
5. The solid material remaining from step 4 is freeze dried for use in topical preparations.
6. The liquid in the container is measured and freeze dried.
7. The freeze dried material resulting from step 6 is reconstituted to its original volume with PBSA.
8. Further dilutions may be made with PBSA in order to prepare the final medication solution.

While certain preferred embodiment of the invention have been described herein, the invention is not to be construed as so limited, except to the extent that such limitations are found in the claims.

What is claimed is:

1. A process for extracting an active principal from an animal material found in nature, said process comprising:
   (a) providing an animal material in a finely divided form suitable for extraction;
   (b) extracting the finely divided animal material in an extraction zone using a solvent to produce a rich solvent and an extract residue;
   (c) fermenting a fermentation feed comprising the rich solvent to produce a fermentation broth comprising a fermentation liquid and a fermentation residue;
   (d) separating the fermentation liquid from the fermentation residue;
   (e) concentrating the fermentation liquid to produce a concentrate;
   (f) extracting the extract residue using a solvent to produce a second rich solvent and a second extract residue;
   (g) extracting the second extract residue using a solvent to produce a third rich solvent and a third extract residue; and
   (h) combining the second rich solvent and the third rich solvent together with the rich solvent to form the fermentation feed.

2. A process as in claim 1 wherein the fermentation feed contains insoluble oils, said process further comprising
separating insoluble oils from the fermentation feed prior to the fermentation step to produce a deoiled fermentation feed.

3. A process as in claim 1 further comprising
concentrating the fermentation liquid by freeze drying to produce the concentrate.

4. A process as in claim 1 wherein the concentrate is in the form of a solid or semi solid material.

5. A process as in claim 1 wherein the solvent comprises a mixture of ethanol and water.

6. A process as in claim 1 wherein the solvent comprises phosphated buffered saline alcohol solution.

7. A process as in claim 6 wherein the solvent contains water, ethanol, and chlorides and phosphates of sodium and potassium.

8. A process as in claim 1 further comprising bringing yeast together with the fermentation feed.

9. A process as in claim 8 further comprising bringing a nutrient medium together with the fermentation feed.

10. A process as in claim 9 wherein the nutrient medium comprises yeast extract, peptone, magnesium salts, and glucose.

11. A process as in claim 10 wherein the nutrient medium further comprises phosphated buffered saline alcohol solution.

12. A process as in claim 10 wherein the nutrient medium further comprises water, ethanol, and chlorides and phosphates of sodium and potassium.

13. A process as in claim 9 wherein the nutrient medium comprises a fermentable sugar.

14. A process as in claim 9 wherein gas is produced during the fermenting of the fermentation feed, said process further comprising continuing fermenting until the production of gas substantially ceases.

15. A process for extracting an active principal from an animal material found in nature, said process comprising:
   (a) providing an animal material in a finely divided form suitable for extraction;
   (b) extracting the finely divided animal material in an extraction zone using a solvent to produce a rich solvent and an extract residue;
   (c) fermenting a fermentation feed comprising the rich solvent to produce a fermentation broth comprising a fermentation liquid and a fermentation residue;
   (d) separating the fermentation liquid from the fermentation residue;
   (e) concentrating the fermentation liquid to produce a concentrate; and
   (f) incinerating the extract residue.

16. A process for extracting an active principal from an animal material found in nature, said process comprising:
   (a) providing an animal material in a finely divided form suitable for extraction;
   (b) extracting the finely divided animal material in an extraction zone using a solvent to produce a rich solvent and an extract residue;
   (c) fermenting a fermentation feed comprising the rich solvent to produce a fermentation broth comprising a fermentation liquid and a fermentation residue;
   (d) separating the fermentation liquid from the fermentation residue;
   (e) concentrating the fermentation liquid to produce a concentrate; and
   (f) incinerating the fermentation residue to produce an ash.

17. A process as in claim 16 further comprising calcining the ash to form calcined ash containing salts.

18. A process as in claim 17 further comprising extracting the salts from the calcined ash to form an aqueous salt-containing medium.

19. A process as in claim 18 further comprising combining the aqueous salt-containing medium with the fermentation liquid.

20. A process for extracting an active principal from an animal material found in nature, said process comprising:
   (a) providing an animal material in a finely divided form suitable for extraction;
   (b) extracting the finely divided animal material in an extraction zone using a solvent to produce a rich solvent and an extract residue;
   (c) fermenting a fermentation feed comprising the rich solvent to produce a fermentation broth comprising a fermentation liquid and a fermentation residue;
   (d) separating the fermentation liquid from the fermentation residue;
   (e) pre-freezing the fermentation liquid to prepare a sublimation feed comprising ice;
   (f) freeze drying the sublimation feed to remove the ice from the sublimation feed and form a low moisture content product and alcoholic vapors; and (g) finish drying the low moisture content product under isothermal desorption conditions.

21. A process as in claim 20 further comprising condensing the alcoholic vapors to form a liquid and recycling the liquid to the extraction zone.

22. A process as in claim 1 wherein a macerated animal material is extracted and the solvent comprises phosphated buffered saline alcohol solution.

23. A process as in claim 1 wherein the extract residue, the second extract residue, and the third extract residue are produced by centrifugation.

24. A process as in claim 1 wherein the fermentation residue is produced by centrifugation.

* * * * *